US00PP30400P2

(12) United States Plant Patent
Ammerlaan

(10) Patent No.: US PP30,400 P2
(45) Date of Patent: Apr. 16, 2019

(54) ***ECHEVERIA* PLANT NAMED 'OVPEARLS04'**

(50) Latin Name: *Echeveria shaviana*
Varietal Denomination: OVPEARLS04

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 15/732,869

(22) Filed: Jan. 5, 2018

(30) Foreign Application Priority Data

Oct. 12, 2017 (QZ) ..... PBR 2017/2562

(51) Int. Cl.
*A01H 5/12* (2018.01)

(52) U.S. Cl.
USPC ..... Plt./373

(58) Field of Classification Search
USPC ..... Plt./373
CPC ..... A01H 5/12
See application file for complete search history.

*Primary Examiner* — Keith O. Robinson
(74) *Attorney, Agent, or Firm* — Samuel R. McCoy, Jr.

(57) ABSTRACT

A new and distinct variety of *Echeveria* plant named 'OVPEARLS04' which is characterized by a compact globular plant form with an abundance of foliage which is tightly held in a basal rosette, flabellate foliage with a heavily undulated praemorse apex, and heavily pruinose foliage which gives the foliage a purple hue. The new variety has shown to be uniform and stable in the resulting generations from asexual propagation.

4 Drawing Sheets

Latin name of the genus and species: The Latin name of the genus and species of the novel variety disclosed herein is *Echeveria shaviana.*

Variety denomination: The inventive variety of *Echeveria* disclosed herein has been given the variety denomination 'OVPEARLS04'.

CROSS REFERENCE TO RELATED APPLICATIONS

This application claims priority to the Community Plant Variety Rights application number 2017/2562, filed on Oct. 12, 2017, which is herein incorporated by reference.

BACKGROUND OF THE INVENTION

Parentage: 'OVPEARLS04' is a naturally-occurring, whole-plant mutation of an unnamed *Echeveria shaviana* plant (not patented) which was discovered by the inventor in March of 2009 at a commercial greenhouse in Bleiswijk, the Netherlands. The mutation was noted for its purple foliage and strongly undulated leaf apices.

Asexual Reproduction: Asexual reproduction of the new cultivar 'OVPEARLS04', by way of rooting leaf cuttings, was first initiated in March of 2009 at the inventor's commercial greenhouse in Bleiswijk, the Netherlands. Through eight subsequent generations, the unique features of this cultivar have proven to be stable and true to type.

SUMMARY OF THE INVENTION

The cultivar 'OVPEARLS04' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS04'. These characteristics in combination distinguish 'OVPEARLS04' as a new and distinct *Echeveria* cultivar:

1. 'OVPEARLS04' exhibits a compact globular plant form; and
2. 'OVPEARLS04' exhibits an abundance of foliage, held upright, and tightly held in a basal rosette; and
3. 'OVPEARLS04' exhibits flabellate foliage with a heavily undulated, praemorse apex; and
4. 'OVPEARLS04' exhibits heavily pruinose foliage which gives the foliage a purple hue.

BOTANICAL DESCRIPTION OF THE PLANT

Figure 1:
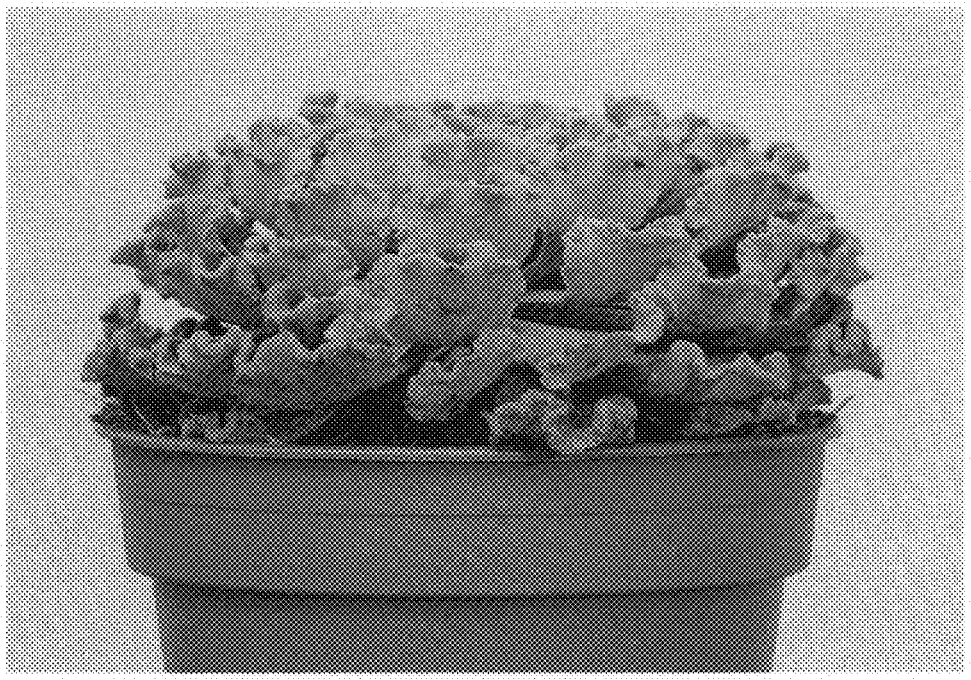
FIG. 1 illustrates, as nearly true as it is reasonably possible to make the same in color photographs of this type, an exemplary plant of 'OVPEARLS04' grown in a commercial greenhouse in Bleiswijk, the Netherlands. This plant is approximately 1 year old, shown planted in a 17 cm container.
Figure 2:
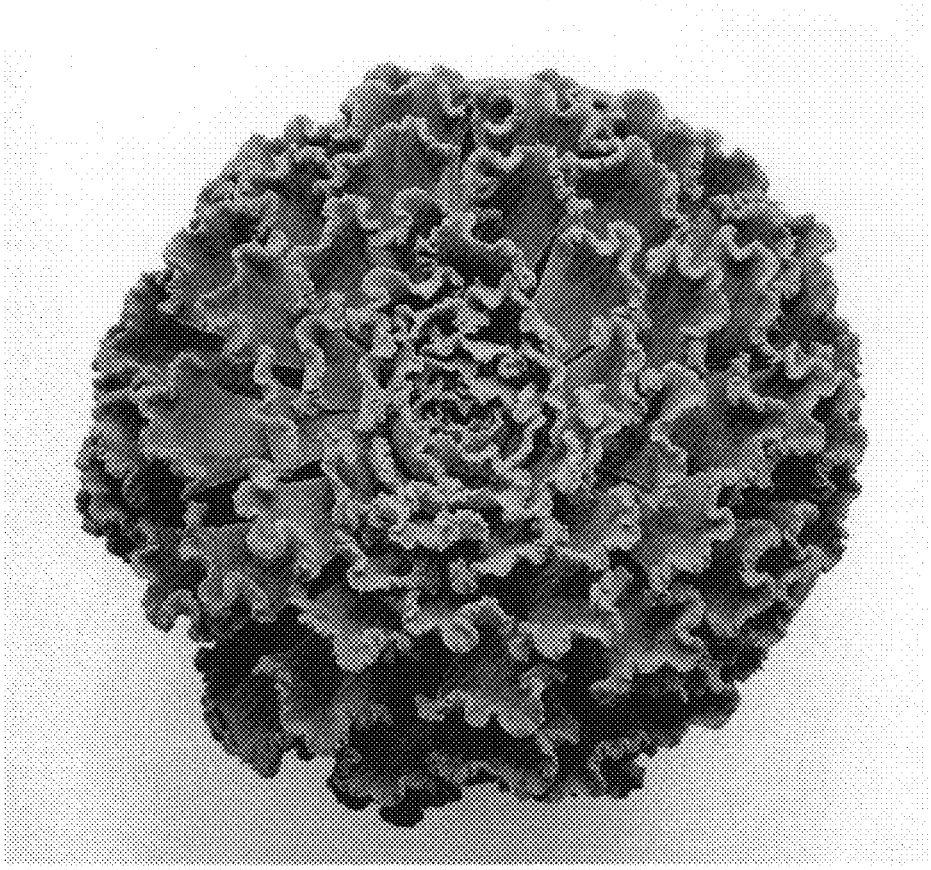
FIG. 2 illustrates, as nearly true as it is reasonably possible to make the same in color photographs of this type, the typical foliage arrangement of 'OVPEARLS04'.
Figure 3:
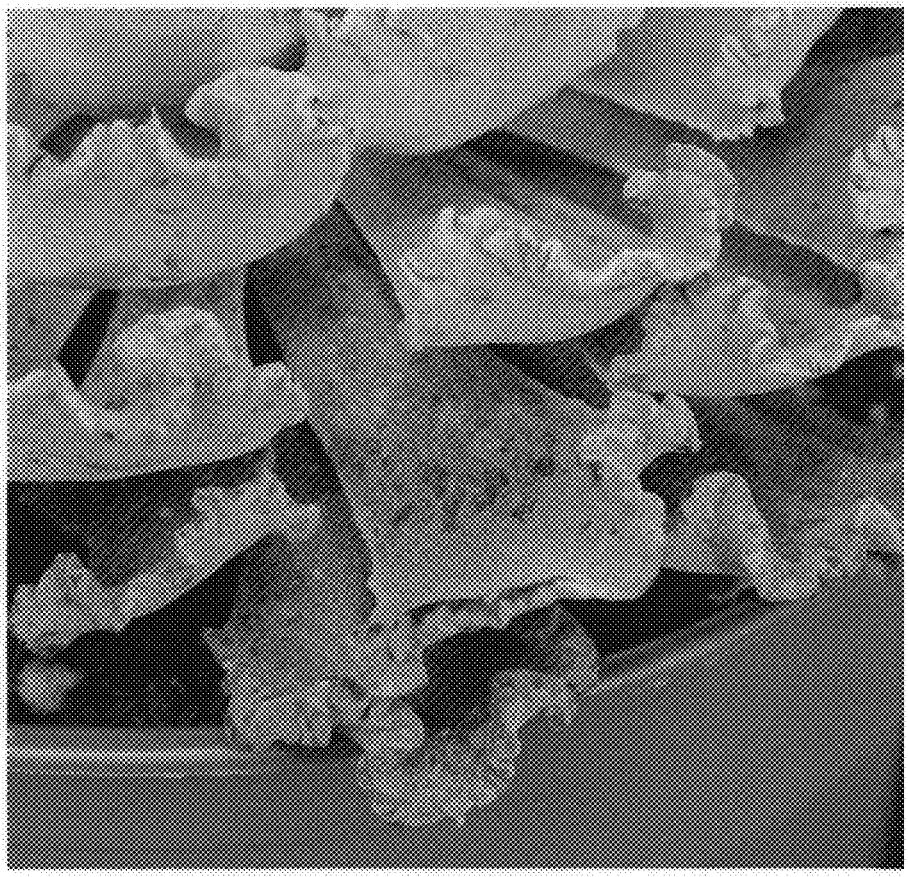
FIG. 3 illustrates, as nearly true as it is reasonably possible to make the same in color photographs of this type, the adaxial surface of the mature foliage 'OVPEARLS04'.
Figure 4:
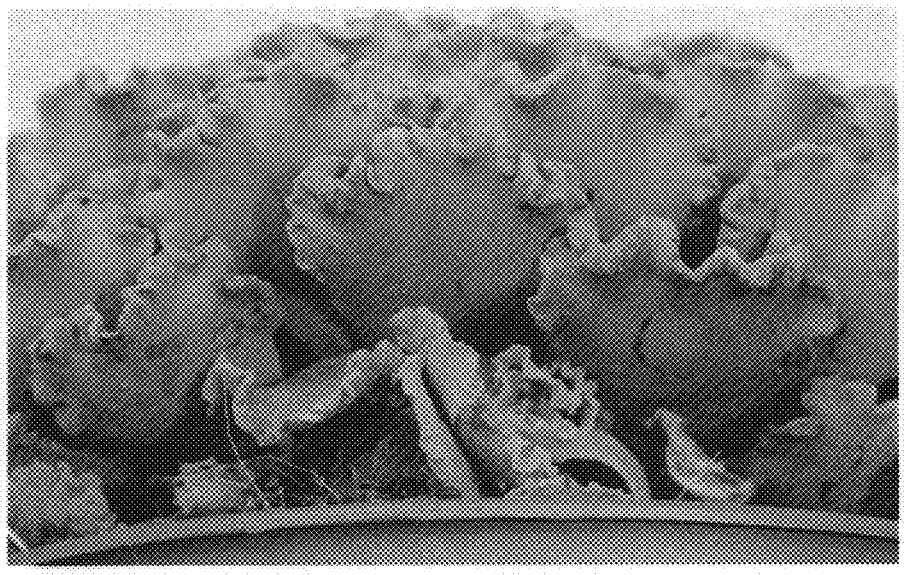
FIG. 4 illustrates, as nearly true as it is reasonably possible to make the same in color photographs of this type, the abaxial surface of the mature foliage 'OVPEARLS04'.

The following observations and measurements made in October of 2017 describe averages from a sample set of six specimens of 1 year old 'OVPEARLS04' plants grown in 17 cm nursery containers at commercial greenhouse in Bleiswijk, the Netherlands. Plants were produced using conventional greenhouse production protocols for *Echeveria* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS04' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVPEARLS04' and a comparison with the parent and closest known comparator is provided below.

Plant description:

*Growth habit*.—Succulent perennial with foliage growing in a compact, non-branched basal rosette.

*Plant form*.—Globular.

*Height from soil level to top of foliar plane*.—9.2 cm.

*Plant spread*.—Average of 17.4 cm.

*Growth rate*.—Moderate.

*Plant vigor*.—Moderate.

*Propagation*.—Type — Leaf cuttings. Time to initiate rooting — Approximately 5 weeks at an approximate temperature of 21 degrees Celsius. Crop time — Approximately 1 year to produce a marketable plant in a 12 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—No stems or branches; leaves arranged in a basal rosette.

Foliage:

*Arrangement*.—Rosette.

*Division*.—Simple.

*Attachment*.—Sessile.

*Quantity*.—Approximately 97 leaves per rosette.

*Shape*.—Thick, succulent leaves which are narrowly flabellate.

*Dimensions*.—7.5 cm long, 3.3 cm wide, and 0.4 cm thick, on average.

*Aspect*.—Flat. Distal portion of the leaf is curled upward at an approximate angle of 45 degrees to the proximal portion of the leaf.

*Attitude*.—Leaves are held upright and outward.

*Apex*.—Praemorse and strongly undulated.

*Base*.—Narrowly long cuneate.

*Margin*.—Entire; strongly undulated towards the apex, otherwise not undulated.

*Pubescence, texture and luster of the adaxial surface*.—Glabrous, smooth, and matte; heavily pruinose, colored greyed-green, nearest to in between RHS 188A and N189C.

*Pubescence, texture and luster of the abaxial surface*.—Glabrous, smooth, and matte; heavily pruinose, colored greyed-green, nearest to RHS 188A.

*Color*.—Juvenile foliage, adaxial surface; pruinose removed — Nearest to in between yellow-green, RHS 148A, and greyed-green, RHS 194A; fading to yellow-green towards the apex. Juvenile foliage, abaxial surface; pruinose removed — Nearest to in between green, RHS 138B, and yellow-green, RHS 147C. Mature foliage, adaxial surface; pruinose removed — Yellow-green, nearest to RHS 147A, and lighter towards the base, nearest to RHS 146C. Mature foliage, abaxial surface; pruinose removed — Yellow-green, nearest to RHS 147B, and lighter towards the base, nearest to RHS 146C.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANT

Plants of the new cultivar 'OVPEARLS04' differ from the parent, an unnamed *Echeveria shaviana* plant (not patented) in the following characteristics described in Table 1 below.

TABLE 1

| Characteristic | 'OVPEARLS04' | The parent. |
|---|---|---|
| Growth habit. | More compact. | Less compact. |
| Foliage attitude. | Foliage is more upright. | Foliage is less upright. |
| Foliage aspect. | Distal portion of the leaf is more curled upward. | Distal portion of the leaf is less curled upward. |
| Foliage length. | Foliage is shorter. | Foliage is longer. |
| Foliage apex. | More strongly undulated. | Less undulated. |
| General coloration of the foliage. | Greyed-green, with a stronger purple hue, | Greyed-green, with a weaker purple hue. |

COMPARISONS WITH THE CLOSEST KNOWN COMPARATOR

Plants of the new cultivar 'OVPEARLS04' differ from the species *Echeveria* 'Cheyenne' (not patented), which is the closest known comparator, in the following characteristics described in Table 2 below.

TABLE 2

| Characteristic | 'OVPEARLS04' | 'Cheyenne' |
|---|---|---|
| Growth habit. | More compact. | Less compact. |
| Foliage attitude. | Foliage is more upright. | Foliage is less upright. |
| Foliage aspect. | Distal portion of the leaf is more curled upward. | Distal portion of the leaf is less curled upward. |
| Foliage length. | Foliage is shorter. | Foliage is longer. |
| General coloration of the foliage. | Greyed-green, with a stronger purple hue. | Greyed-green, with a weaker purple hue. |

That which is claimed is:

1. A new and distinct variety of *Echeveria* plant named 'OVPEARLS04', substantially as described and illustrated herein.

* * * * *